(12) United States Patent
Majidi et al.

(10) Patent No.: US 10,757,815 B2
(45) Date of Patent: Aug. 25, 2020

(54) METHOD FOR FABRICATION OF A SOFT-MATTER PRINTED CIRCUIT BOARD

(71) Applicant: CARNEGIE MELLON UNIVERSITY, Pittsburgh, PA (US)

(72) Inventors: Carmel Majidi, Pittsburgh, PA (US); Tong Lu, Pittsburgh, PA (US); Eric J. Markvicka, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 0 days.

(21) Appl. No.: 16/243,475

(22) Filed: Jan. 9, 2019

(65) Prior Publication Data

US 2019/0215965 A1    Jul. 11, 2019

Related U.S. Application Data

(60) Provisional application No. 62/709,177, filed on Jan. 9, 2018.

(51) Int. Cl.

| H05K 1/00 | (2006.01) |
|---|---|
| H05K 1/18 | (2006.01) |
| H05K 1/02 | (2006.01) |
| H05K 3/46 | (2006.01) |
| H05K 1/09 | (2006.01) |
| H05K 3/30 | (2006.01) |
| H05K 3/06 | (2006.01) |
| A61N 1/00 | (2006.01) |
| H05K 3/02 | (2006.01) |

(52) U.S. Cl.
CPC ............ *H05K 1/189* (2013.01); *H05K 1/028* (2013.01); *H05K 1/0283* (2013.01); *H05K 1/09* (2013.01); *H05K 1/092* (2013.01); *H05K 1/181* (2013.01); *H05K 1/185* (2013.01); *H05K 3/06* (2013.01); *H05K 3/30* (2013.01); *H05K 3/4644* (2013.01); *A61N 1/00* (2013.01); *H05K 3/027* (2013.01); *H05K 2201/0133* (2013.01); *H05K 2201/0248* (2013.01); *H05K 2201/083* (2013.01); *H05K 2203/107* (2013.01); *H05K 2203/128* (2013.01); *H05K 2203/1461* (2013.01)

(58) Field of Classification Search
USPC ......................................................... 361/749
See application file for complete search history.

(56) References Cited

U.S. PATENT DOCUMENTS

| 9,872,390 B1 * | 1/2018 | Holbery ............. H01L 23/5387 |
| 2015/0253602 A1 * | 9/2015 | Kim .................. G02F 1/136204 |
| | | 349/50 |

* cited by examiner

*Primary Examiner* — Andargie M Aychillhum

(57) ABSTRACT

A fabrication process for soft-matter printed circuit boards is disclosed in which traces of liquid-phase Ga—In eutectic (eGaIn) are patterned with UV laser micromachining (UVLM). The terminals of the elastomer-sealed LM circuit connect to the surface mounted chips through vertically-aligned columns of eGaIn-coated ferromagnetic microspheres that are embedded within an interfacial elastomer layer.

10 Claims, 4 Drawing Sheets

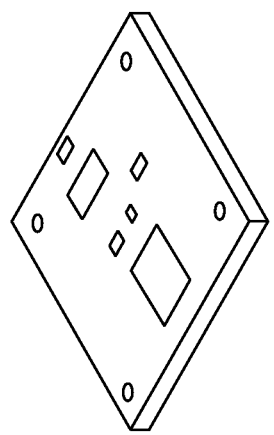
FIG. 3A
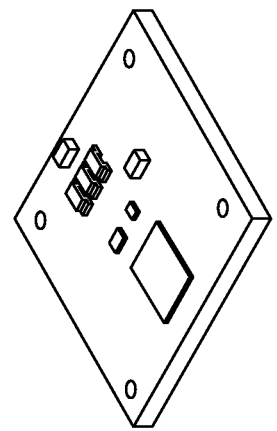
FIG. 3B
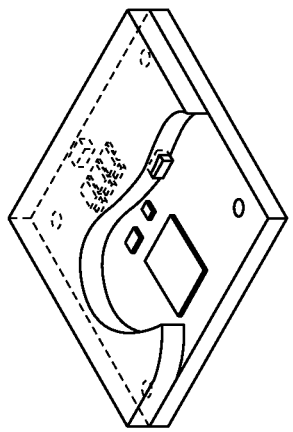
FIG. 3C
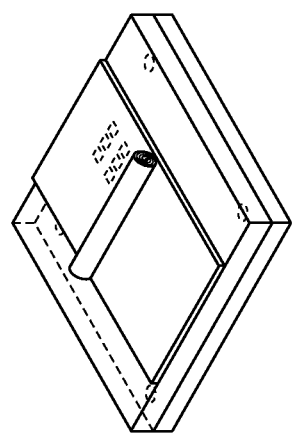
FIG. 3D
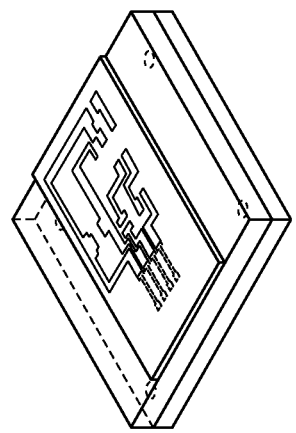
FIG. 3E
FIG. 3F

METHOD FOR FABRICATION OF A SOFT-MATTER PRINTED CIRCUIT BOARD

RELATED APPLICATIONS

This application claims the benefit of U.S. Provisional Patent Application No. 62/709,177, filed Jan. 9, 2018.

GOVERNMENT RIGHTS

This invention was made with government support under NASA No. NNX14AO49G, and ONR Nos. N00014-14-1-0778 and N00014-16-1-2301. The government has certain rights in this invention.

BACKGROUND OF THE INVENTION

Skin-mounted electronics for wearable computing and health monitoring require stretchable circuits that match the mechanical properties of soft natural tissue. Current approaches include so-called "deterministic architectures" in which mechanical compliance is introduced through geometry, for example, PANI or Ag—Ni alloy coated on a woven fabric or thin metal interconnects with serpentine or pre-buckled wavy geometries. Because the conductive materials are intrinsically rigid (elastic modulus $\geq 1$ GPa) and inextensible, stretchable functionality must be engineered through microscale geometric design and cleanroom fabrication.

Another popular approach is to use conductive polymers and composites that are intrinsically soft and deformable. Polyurethanes (PU), polydimethylsiloxane (PDMS), polyacrylates, fluoropolymers, and styrene ethylene butylene styrene copolymer (SEBS) are typically used as the carrier medium. To be conductive, they are typically embedded with percolating networks of rigid metallic nano/microparticles or carbon allotropes (e.g. MWCNT, graphene) or are grafted with polyaniline, ionomers (e.g. PEDOT:PSS) and other conductive polymer groups.

While promising for low-load or moderate-strain applications, these composites are typically more rigid and less elastic than homogenous elastomers, stretchable elastane fabrics, or natural biological tissue. Nonetheless, they have adequate mechanical properties for electronic skin applications and can be patterned using a variety of rapid fabrication methods.

Liquid metal (LM)-based circuits represent a versatile alternative for stretchable electronics that bypass some of the limitations of deterministic architectures and polymer composites. Ga-based LM alloys like Ga—In eutectic (eGaIn; 75% Ga and 25% In, by wt.) and Ga—In—Sn (Galinstan; 68% Ga, 22% In, 10% Sn) are particularly attractive because of their low viscosity, high electrical conductivity, low melting point, low toxicity, and negligible vapor pressure. When encapsulated in a soft elastomer, for example, PDMS, liquid-phase traces of Ga-based alloy can provide highly robust electrical connectivity between solid state elements within a circuit and enable extreme elastic deformability. Another feature of Ga-based LM alloys is that, in $O_2$-rich environments like air, they form a self-passivating surface layer of $Ga_2O_3$ (thickness ~1-3 nm) that dramatically reduces surface tension and allows patterned traces to hold their shape. This oxidation and moldability has enabled eGaIn to be patterned with a variety of techniques based on stencil lithography, selective wetting, reductive patterning, microcontact printing, jetting, and 3D direct-write printing.

Since the mid-2000s, eGaIn microfluidic systems have been engineered for a broad range of applications. In the last couple of years, this includes continued efforts in sensing and electromechanical transducers, force characterization for medical endoscopy, reconfigurable metamaterials and radio antennae that exhibit tunable operating frequency and enhanced range.

Despite their extraordinary potential, progress in LM electronics is currently limited by methods for integration with MOSFETs, microprocessors, chipsets, cable adapters, and other solid-state technologies (SSTs). Recent efforts with so-called dual-trans printing and z-axis conductive elastomer have successfully addressed integration but only with millimeter-scale pins and traces.

Successful integration of LM-based circuits and microscale SSTs requires processing techniques that are compatible with conventional PCB manufacturing, enable reliable interfacing between the terminals of the LM circuit and I/O pins of packaged electronics, and allow for planar circuit features with dimensions below 100 μm.

When encapsulated in elastomer, micropatterned traces of Ga-based liquid metal (LM) can function as elastically deformable circuit wiring that provides mechanically robust electrical connectivity between solid state elements (e.g. transistors, processors, sensor nodes). However, LM-microelectronics integration is currently limited by challenges in rapid fabrication of LM circuits and the creation of vias between circuit terminals and the I/O pins of packaged electronics.

SUMMARY OF THE INVENTION

The invention includes printed circuit boards (PCBs) that are soft and stretchable and methods for producing them. These soft-matter PCBs are composed of a liquid metal (LM) circuit printed on an elastomer ("rubber") substrate. The traces of the LM circuit are patterned using a UV laser micromachining (UVLM) system. After patterning, the circuit is sealed with a thin coating of "z-axis" anisotropic elastomer that is conductive only through its thickness (i.e., in the z-axis direction). The z-axis elastomer is composed of conductive vertically-aligned columns of ferromagnetic microparticles that are coated with Ag and a thin layer of LM alloy. These conductive columns function as vias for forming electrical connections between the embedded LM traces and surface mounted electronics.

The invention also includes the fabrication of LM circuits with UVLM patterning, including a technique for using a UV laser to create circuits of liquid metal and the use of a layer of Z-axis elastomer that contains vertically-aligned columns of LM-coated microparticles which are only conductive through the thickness of the layer, to create vias between embedded circuit traces and surface mounted electronics.

The resulting circuit is naturally soft and flexible and can conform to the skin without requiring significant attachment forces. An example potential application includes an elastomeric band that contains a surface-mounted pulse oximetry unit for reflective photoplethysmogram (PPG) recordings. The PPG waveforms can be used to non-invasively measure blood oxygenation saturation and heart rate, which in turn can be used for tracking physical activity and monitoring a broad range of health conditions.

BRIEF DESCRIPTION OF THE DRAWINGS

FIG. 3A-F shows the steps of the fabrication process of the soft-matter PCB in accordance with the invention.

DETAILED DESCRIPTION

The above challenges are addressed via a unique layup for LM-based soft-matter electronics using innovations in materials selection and processing.

The term liquid metal, as used herein, refers to any metal or metal alloy that is in the liquid state, including, but not limited to, Ga-based alloys such as eutectic Ga—In (eGaIn) and Ga—In—Sn (Galinstan).

The term zPDMS, as used herein, refers to liquid metal-coated microspheres suspended in a cured elastomer, preferably PDMS, produced as described below, wherein the microspheres comprise ferromagnetic microspheres having a liquid metal, for example, Ag-coated $FE_2O_3$ particles having an eGaIn coating. The microspheres are arranged in vertically-oriented columns, such that a layer of zPDMS is anisotropically conductive only in the direction of the z-axis.

Figure 1A:
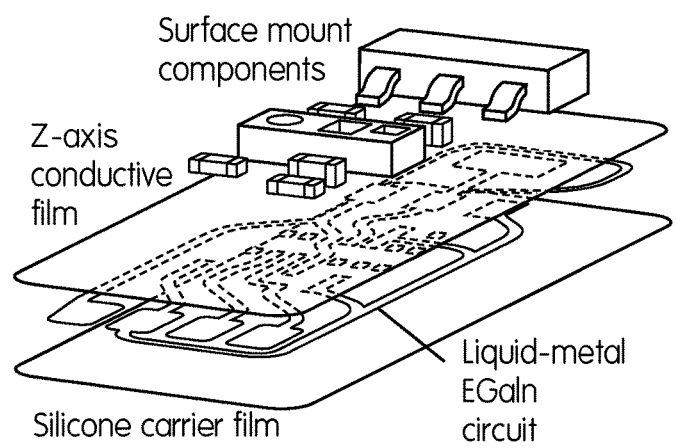
FIG. 1A shows an exemplary soft-matter printed circuit board an exploded form fabricated in accordance with the invention.
Figure 1B:
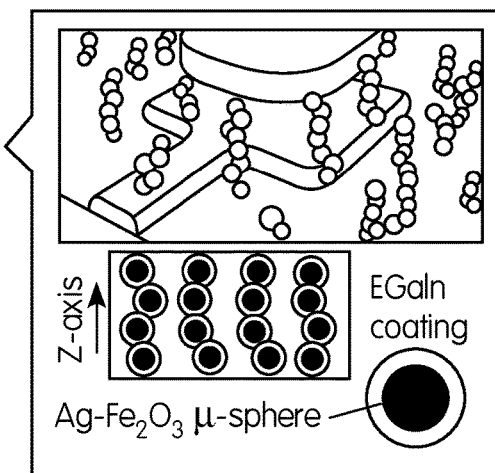
FIG. 1B shows vertically aligned columns of Ag—$Fe_2O_3$ microparticles coated in eGaIn forming z-axis vias between LM trace terminals and surface-mounted components of the PCB of FIG. 1A.

As shown in FIG. 1A, a UV laser micromachining (UVLM) system is used to pattern a coating of LM on a polymer substrate to form circuit paths. In preferred embodiments, the coating of LM may be approximately 20 µm in thickness. The UVLM-patterned eGaIn circuits can interface with surface-mounted SSTs using an anisotropically conductive "z-axis film" composed of vertically-aligned columns of eGaIn-coated Ag—$Fe_2O_3$ microspheres embedded in a PDMS matrix, as shown in FIG. 1B, which serve as vias between the SSTs and the UVLM-patterned eGaIn circuit. In contrast to conventional z-axis films with "dry" ferromagnetic microparticles, the LM-coating allows for electrical connectivity even as the rigid microspheres separate under mechanical deformations induced by circuit bending, compression, stretching, or twisting.

Figure 2:
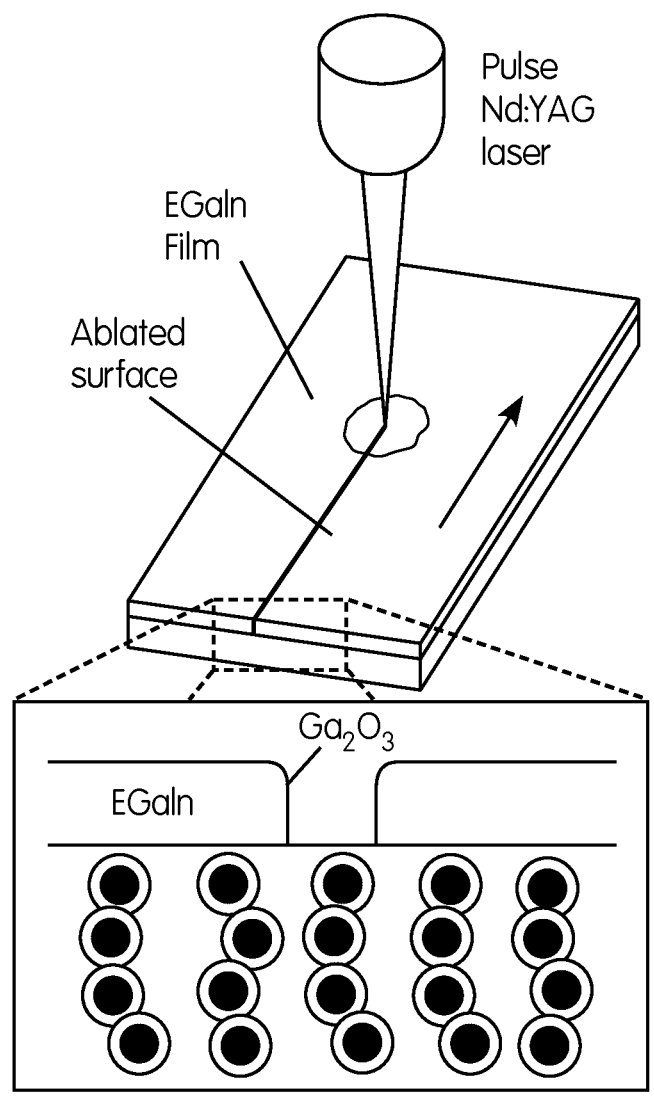
FIG. 2 is an illustration of eGaIn being patterned using the UVLM process. The inset shows a $Ga_2O_3$ passivation layer which is necessary to hold the shape of the LM circuit.

As shown in FIG. 2, a Nd:YAG laser with 355 nm wavelength, 200 kHz pulse rate, and 15 µm diameter beam that is capable of direct photophysical ablation of metal may be used to pattern the eGaIn film to form circuit paths. Using a 1 W beam power, the liquid metal features can be reliably patterned with planar dimensions of 50 µm. In contrast, prior art attempts at eGaIn patterning with a $CO_2$ laser required indirect material expulsion through vapor recoil force that limits the minimum feature size to ~250 µm.

As with eGaIn stencil lithography and additive manufacturing, the ability to laser pattern eGaIn on an elastomeric substrate depends on the formation of a self-passivating, nanometer-thin $Ga_2O_3$ "skin", shown in the inset of FIG. 2. The oxide skin allows the patterned liquid metal to hold its shape after laser ablation and during deposition of an elastomer seal. This feature of liquid moldability is critical for extending conventional UVLM PCB prototyping to Ga-based LM alloys. Combining UVLM processing with liquid metal and z-axis connectivity allows for a versatile method to produce elastically deformable electronics that are mechanically robust and compatible with natural human tissue.

FIG. 3A-F shows the steps in the fabrication process of a soft-matter PCB with embedded LM wiring in accordance with this invention.

As shown in FIG. 3A, a layer of PDMS (for example, 10:1 base-to-curing agent ratio) is applied on a glass substrate by spin coating (KW4A, SPI) at 1500 RPM for 10 s, or by other means, and then cured. Preferably, the PDMS will be cured at 100° C. for 20 min.

Next, a polymer film is placed on top of the PDMS layer and the film is patterned using the UVLM to create placement openings for the rigid integrated circuits (ICs), as well as fiducials for alignment within the UVLM. In an alternative embodiment, the PDMS layer may be patterned directly, without the polymer film.

As shown in FIG. 3B, surface mount SSTs are then placed into the openings. The board side of the components may be dipped in polyvinyl acetate (PVA), to adhere the SSTs to the glass substrate. PVA may then be cured, preferably by heating at 70° C. for 5 min on a hotplate. The SSTs are then sealed with a second layer of PDMS (10:1). Multiple sealing layers of PDMS may be applied until the surface mount components are covered. Preferably, the sealing layers are spin-casted (600 RPM, 5 s) and cured (100° C., 20 min).

The SST-embedded elastomer is then peeled from the substrate and placed on the glass disc with the board side of the components exposed, as shown in FIG. 3C. The exposed components are rinsed with deionized water to remove the PVA.

After drying, as shown in FIG. 3D, a layer of zPDMS is deposited on top of the exposed SSTs. Preferably, the zPDMS is deposited by spin coating at 1500 RPM for 10 s; KW-4A, SPI) and cured on top of a flat magnet (for example, ~1448 Gauss, 2"×2"×¼" NdFeB). Preferably, the zPDMS is cured at 100° C. for 20 min. Curing the zPDMS in the presence of the magnetic field causes the eGaIn-coated ferromagnetic microspheres to arrange in vertically-aligned columns, which will become vias between the LM etched circuit and the contacts of the SSTs. It should be noted that the zPDMS layer is only electrically conductive in the areas where the vertically aligned columns of microspheres extend through the thickness of the layer. Coating the microspheres with eGaIn prior to mixing with the PDMS allows the zPDMS to physically deform without the vertically-aligned columns of microspheres breaking apart and losing their ability to conduct in the z-axis direction.

As shown in FIG. 3E, a film of eGaIn is then applied on the zPDMS, preferably using a PDMS roller, and then patterned with a UVLM system, as shown in FIG. 3F. Lastly, the LM circuit is sealed in PDMS and released from the glass substrate. Multiple sealing layers of PDMS may be applied by spin-casting at 600 RPM for 5 s, and then cured at 100° C. for 20 min to match the thickness of the SST-embedded elastomer layer.

In a preferred embodiment, the zPDMS may be prepared by mixing 70 wt % of 40 µm diameter Ag-coated $Fe_2O_3$ particles (20% Ag by wt.) with 30 wt % of eGaIn (75 wt % Ga and 25 wt % In) using a mortar and pestle or other means. The microsphere/eGaIn mixture is then mixed at 50 wt % with uncured PDMS (10:1). In alternate embodiments, the microspheres may be composed of any ferromagnetic material, for example, nickel. In alternate embodiments, the microspheres may optionally be coated with silver or other highly conductive materials prior to mixing with eth eGaIn, to improve conductivity.

With the fabrication process shown in FIG. 3A-F, packaged SST chips can be embedded in elastomer and wired together with eGaIn interconnects that share dimensions similar to those of conventional copper PCB traces (≥50 µm width, ≥100 µm spacing). The UV laser-patterned eGaIn traces exhibit properties that are consistent with classical predictions for electrical resistance and capacitance.

The layup and fabrication process shown in FIG. 3A-F was used to produce several representative demonstration circuits that integrate UVLM-patterned traces of eGaIn with packaged SSTs, as shown in FIG. 4A-D. The demonstration circuits are intended to validate the fabrication method and compatibility of materials.

Figure 4A:
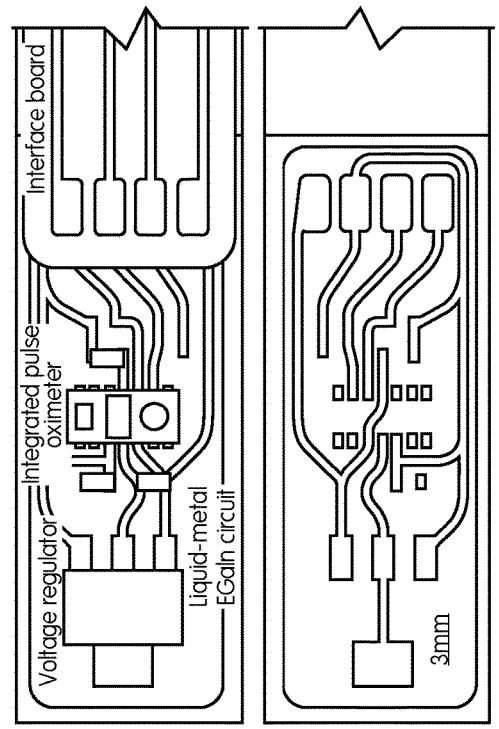
FIG. 4A-D shows examples of representative demonstration circuits used to validate the fabrication method of the present invention.

FIG. 4A shows a demonstration circuit consisting of an array of surface mounted LED and 331Ω resistor chips.

Figure 4B:
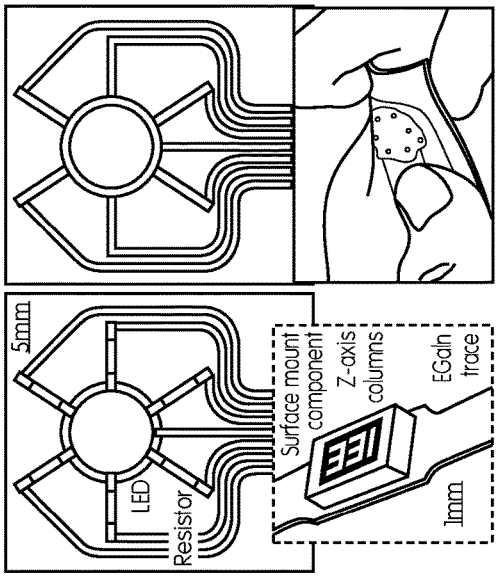
Figure 4C:
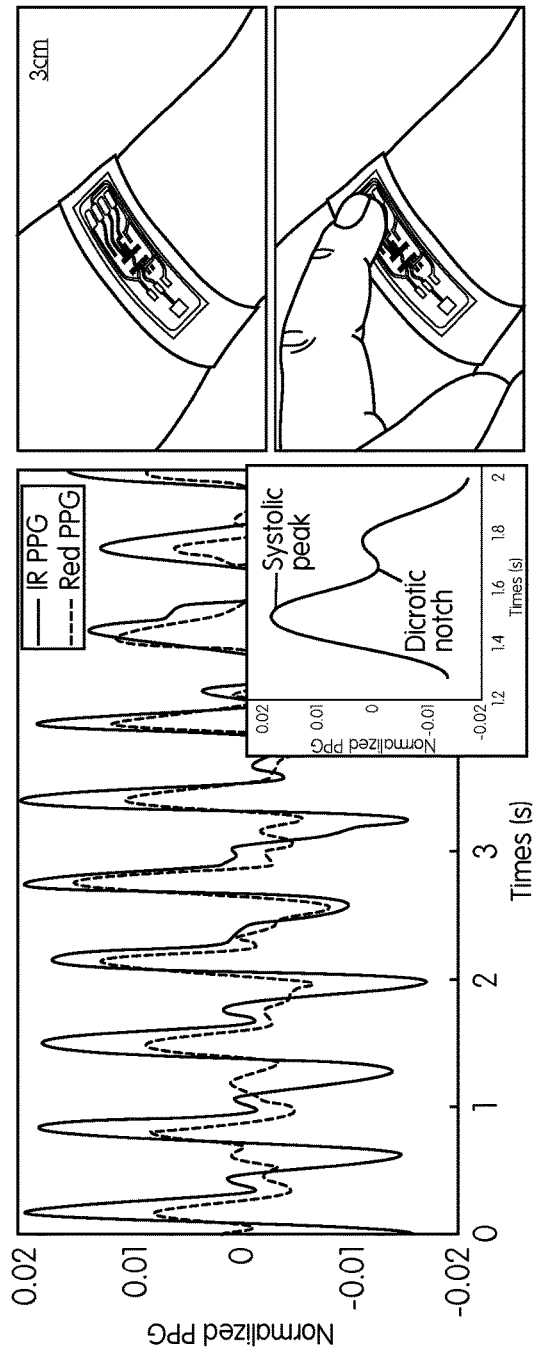
Figure 4D:
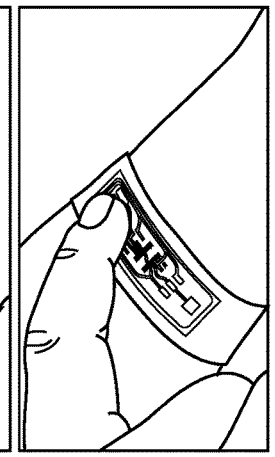

FIG. 4B shows a soft-matter bioelectronic circuit for non-invasive measurements of heart rate (HR) and arterial blood oxygenation ($SpO_2$). The circuit contains an integrated pulse oximetry unit that houses a red and IR LED, photodetector and optics, and a low-noise analog signal processor for reflective PPG waveforms. A flex PCB with Cu traces is used as an interface board that connects the circuit to a battery-powered Bluetooth module that transmit signals to a host computer for signal processing. The device is configured to collect the PPG waveforms at 200 Hz using LED pulse widths of 400 µs and a current of 20.8, as shown in FIG. 4C. With appropriate filtering and calibration, the waveforms can be used to obtain HR from spacing of Systolic peaks and $SpO_2$ by comparing the amplitude (i.e. optical reflection) of IR and red light, which are absorbed differently by oxygenated or deoxygenated hemoglobin within arterial blood. Because the circuit board is intrinsically soft and deformable, the pulse oximetry band can wrap around the wrist and form intimate contact with skin with limited interfacial pressure, as shown in FIG. 4D.

The fabrication technique disclosed herein can be used to produce soft and deformable circuits with liquid metal and UV laser micromachining. To match the mechanical properties of soft natural tissue, the relatively stiff materials typically used in existing PCBs (metal wiring, soldered connections, and glassy polymer substrate) are replaced with liquid-phase metal alloy and elastomer. This biomechanically compatible "soft-matter" PCB can be rapidly produced using the same commercial UVLM system used for conventional electronics prototyping. Because the circuit is composed entirely of soft and deformable material, fabrication does not depend on a limited selection of geometric patterns or the specialized microfabrication techniques required for thin-film metal circuits with deterministic architectures. In this respect, the method represents a relatively inexpensive, scalable, and user-accessible alternative that complements previous achievements in stretchable and thin-film electronics based on cleanroom lithography.

The intrinsic compliance of the soft-matter PCB is of particular importance in wearable bioelectronics and computing. For these applications, mechanical impedance mismatch can constrain natural body motion or cause irritation, discomfort, or tissue damage due to interfacial stress concentrations. Impedance matching is especially critical in optical or electrode-based bioelectronics applications, such as pulse oximetry, that depend on intimate contact with the skin for accurate physiological measurements. Incorporating soft materials, SSTs, and processing steps into a single UVLM-based fabrication method enables the rapid production of customizable wearables. Such systems could be user/patient-specific and capable of physiological sensing for activity, fitness, and health monitoring.

The method of the present invention has been explained in terms of examples utilizing specific equipment and fabrication parameters. It should be realized by one of skill in the art that alternatives in the equipment or variations in the fabrication parameters may be used to produce results that are intended to be within the scope of the invention. Additionally, examples of specific circuits have been provided as a validation of the fabrication method. As further realized by one of skill in the art, the fabrication method is not meant to be limited to these specific applications but may be used to produce circuits intended for any purpose.

We claim:

1. A soft-matter printed circuit board comprising:
   one or more solid state devices suspended in a layer of an elastomeric material such that a board-side of the devices is exposed;
   a layer of an anisotropically conductive substance comprising ferromagnetic microspheres coated with a liquid metal and suspended in a cured elastomeric substance covering the exposed board side of the devices;
   a layer of liquid metal disposed on the layer of an anisotropically conductive substance, the layer of liquid metal having a circuit pattern etched therein.

2. The soft-matter printed circuit board of claim 1 further comprising a sealing layer disposed over the layer of etched liquid metal.

3. The soft-matter printed circuit board of claim 2 wherein the layer of elastomeric material is PDMS.

4. The soft-matter printed circuit board of claim 3 wherein the layer of elastomeric material is disposed on a glass plate.

5. The soft-matter printed circuit board of claim 4 wherein the layer of elastomeric material is coated on the side opposite the glass plate with the ceiling sealing layer comprising an elastomeric material.

6. The soft-matter printed circuit board of claim 4 wherein the board side of the one or more solid state devices is exposed when the layer of elastomeric material is removed from the glass plate.

7. The soft-matter printed circuit board of claim 1 wherein the one or more circuit paths are aligned with appropriate contacts on the solid state devices and wherein the circuit paths and contacts are separated by the layer of an anisotropically conductive substance.

8. The soft-matter printed circuit board of claim 1 wherein the one or more circuit paths are etched in the layer of liquid metal using a UV laser micromachining process.

9. The soft-matter printed circuit board of claim 1 wherein the ferromagnetic microspheres are coated with silver and the liquid metal.

10. The soft-matter printed circuit board of claim 1 wherein the layer of liquid metal is eGaIn.

* * * * *

UNITED STATES PATENT AND TRADEMARK OFFICE
CERTIFICATE OF CORRECTION

PATENT NO. : 10,757,815 B2
APPLICATION NO. : 16/243475
DATED : August 25, 2020
INVENTOR(S) : Carmel Majidi, Tong Lu and Eric J. Markvicka It is certified that error appears in the above-identified patent and that said Letters Patent is hereby corrected as shown below:

In the Claims

Column 6, Claim 5, Line 39; Please replace "plate with the ceiling sealing layer" with --plate with the sealing layer--

Signed and Sealed this
Tenth Day of November, 2020

Andrei Iancu
*Director of the United States Patent and Trademark Office*